United States Patent [19]
Poll

[11] Patent Number: 5,364,407
[45] Date of Patent: Nov. 15, 1994

[54] LAPAROSCOPIC SUTURING SYSTEM

[76] Inventor: Wayne L. Poll, 1139 Sleeping Meadow Dr., New Albany, Ohio 43054

[21] Appl. No.: 215,422
[22] Filed: Mar. 21, 1994
[51] Int. Cl.$^5$ .............................................. A61B 17/04
[52] U.S. Cl. .................................. 606/139; 606/232; 606/224; 24/136 R; 24/518
[58] Field of Search ............... 606/232, 139, 222, 224; 24/136 R, 129 W, 518

[56] References Cited

U.S. PATENT DOCUMENTS

| | | | |
|---|---|---|---|
| 824,556 | 6/1906 | Lowry et al. | 24/136 R |
| 3,802,438 | 4/1974 | Wolvek | 606/232 |
| 3,910,281 | 10/1975 | Kletschka et al. | 606/232 |
| 4,387,489 | 6/1983 | Dudek | 606/232 |
| 4,750,492 | 6/1988 | Jacobs | 606/232 |
| 5,078,731 | 1/1992 | Hayhurst | 606/232 |
| 5,123,913 | 6/1992 | Wilk et al. | 606/232 |
| 5,217,486 | 6/1993 | Rice et al. | 606/232 |
| 5,258,016 | 11/1993 | DiPoto et al. | 606/232 |

Primary Examiner—Stephen C. Pellegrino
Assistant Examiner—Gary Jackson
Attorney, Agent, or Firm—Sidney W. Millard

[57] ABSTRACT

Apparatus for connecting the ends of a suture stitch includes a piston and cylinder combination with one end of the suture secured to the cylinder. The other end of the suture initially includes a needle for penetrating two tissues to be approximated and then passing the needle and its attached suture through aligned openings in the cylinder sidewalls. The portion of the suture passing through the cylinder is trapped therein by the depression of the piston to engage the bottom inside surface of the cylinder which locks that end of the suture in place.

20 Claims, 4 Drawing Sheets

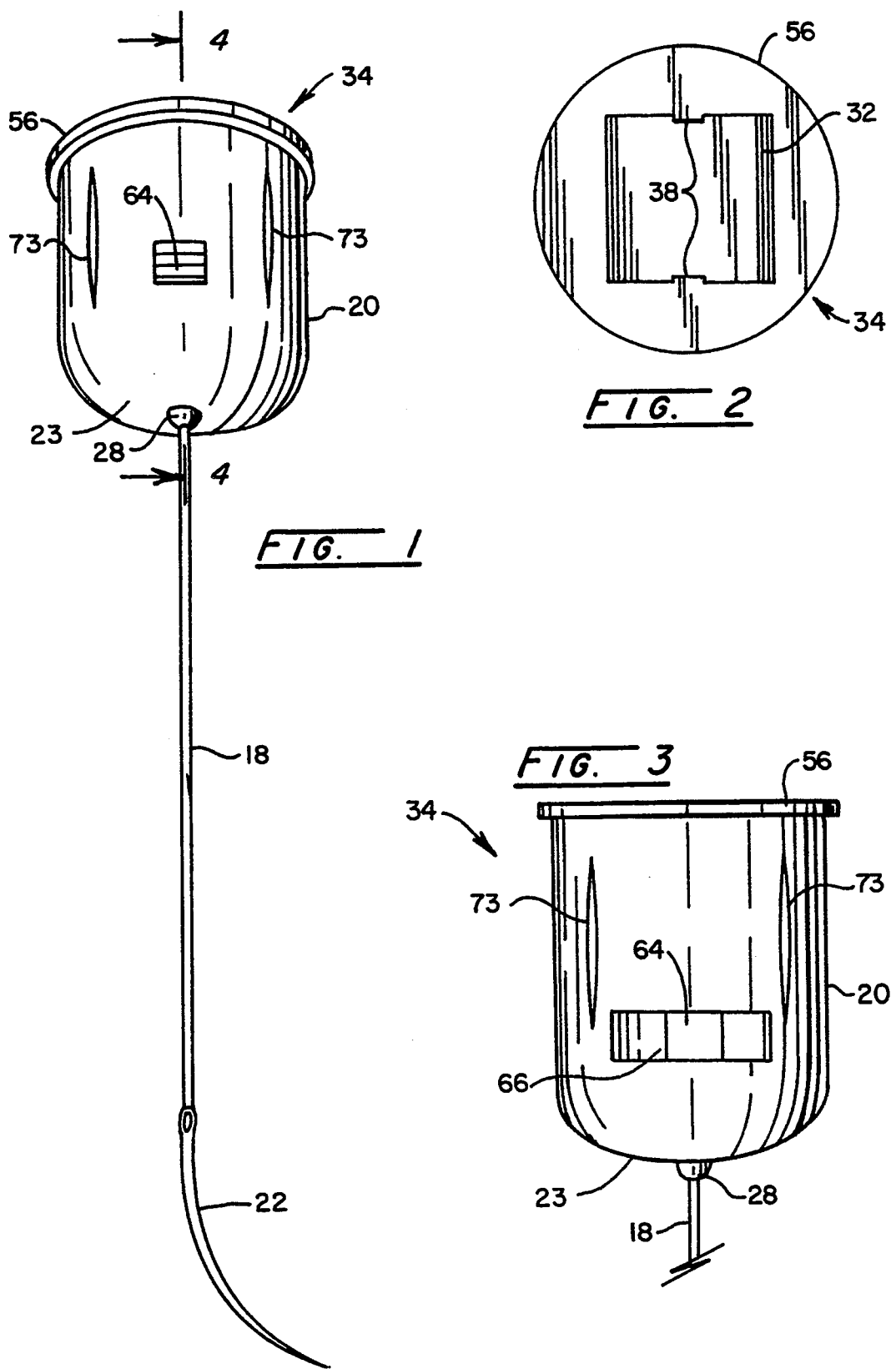

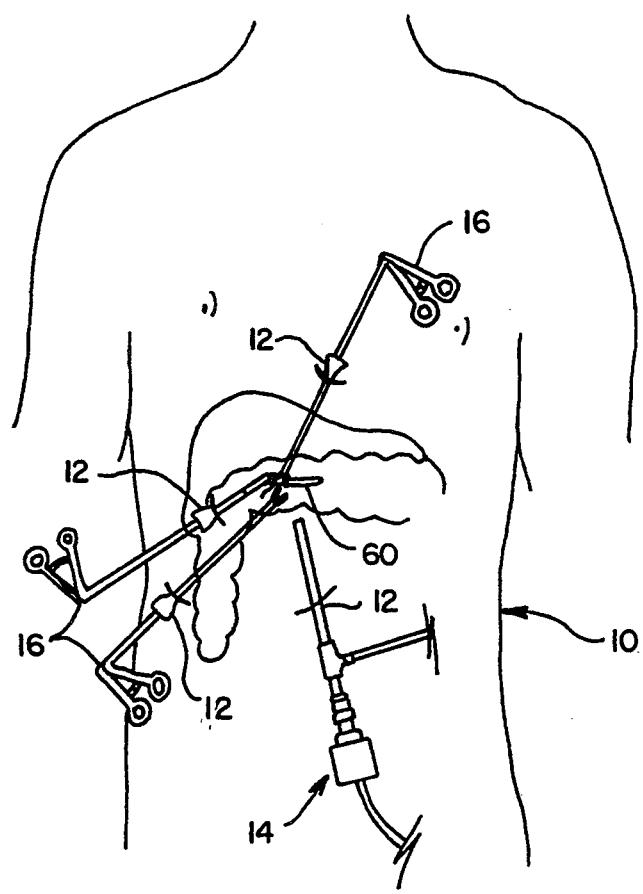
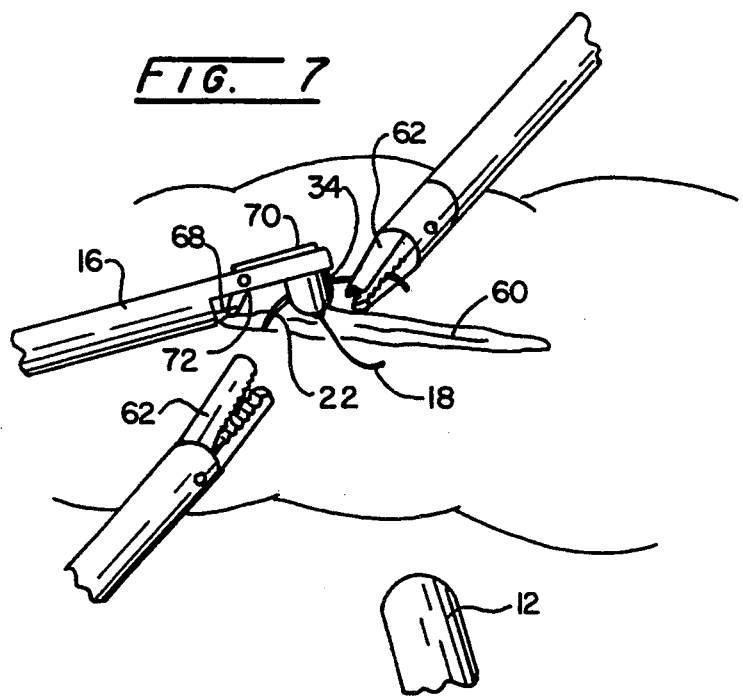

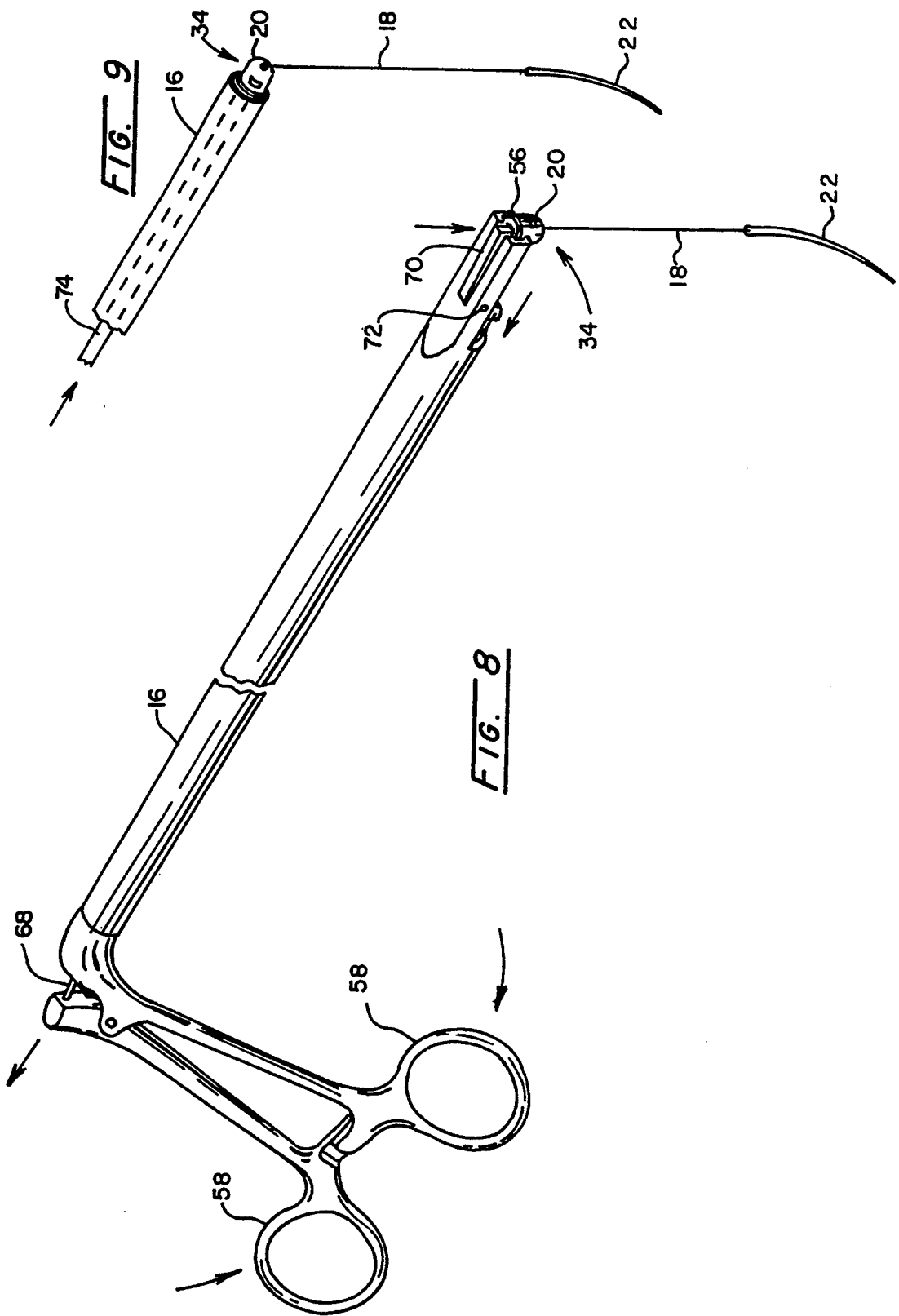

LAPAROSCOPIC SUTURING SYSTEM

FIELD OF THE INVENTION

This invention relates to a piston and cylinder combination for securing the ends of a suture stitch in place without the need for tying a knot in the ends of the suture.

BACKGROUND OF THE INVENTION

Conventional means for closing a wound or approximating tissue includes passing a needle and the suture through the sides of the tissue separation, drawing a tension on the suture to approximate the tissue and tying the ends of the suture together to hold the tissues in place for healing. This procedural sequence is satisfactory when medical personnel are operating on an exterior part of the body. It does not work so conveniently in closing intracorporeal laparoscopic incisions or approximating tissues.

SUMMARY OF THE INVENTION

Intracorporeal laparoscopic suturing is tedious and awkward. Suture placement itself can be mastered and aided considerably by efficient endoscopic needle drivers. Actual tissue approximation through knot tying is a real obstacle. The technique of endoscopic tying is laborious, awkward, and time consuming. Surgeons have worked around this hindrance through the imaginative uses of staples, mesh, and extracorporeal techniques. Staples are not adept at bringing tissues together under any tension whatsoever, and extracorporeal tying is feasible only when a very few sutures need to be placed. In practice, the necessity for intracorporeal tissue approximation through knot tying has rendered some procedures impractical with existing technology.

The biggest problem in securing the ends of a suture together in endosurgery is the inability to precisely manipulate fine threads of suture using instruments with no tactile feedback, all done remotely on two-dimensional television monitors.

This invention eliminates the need for tying knots in the ends of sutures. In the preferred embodiment, one end of the suture is attached to the bottom of the cylinder or housing of a suture lock and the other end of the suture has a needle attached thereto by swedging or other suitable means.

A stitch is formed by passing the needle through the side edges of the tissues to be drawn together and then the needle with the attached suture is passed through diagonally opposed openings in the sidewall of the housing generally perpendicular to the axis of a piston mounted for reciprocation in the housing. Tensioning the suture approximates the tissues and when they are in suitable relationship, the piston is crimped into the housing to trap the needle end of the suture between the bottom of the piston and the bottom inside surface of the housing.

Then the needle may be separated from the suture by snipping the suture immediately adjacent its exit from the sidewall of the housing and the needle may be withdrawn from the cavity from an endoport in conventional fashion.

After the wound has healed, removal of the suture and the lock may be accomplished in conventional fashion. If that is not practical, the body can easily tolerate a permanent implant, much like implantable mesh, dacron, or gortex. Alternatively, the suture and associated lock may be composed of conventional materials which dissolve within the body over time. Overall, the lock is a small device, preferably constructed of biocompatible plastics.

Objects of the invention not understood from the above summary will be clear upon a review of the drawings and a description of the preferred embodiments which follow.

BRIEF DESCRIPTION OF DRAWINGS

FIG. 1 is a perspective view of a suture lock with attached suture and needle according to this invention;

FIG. 2 is a top plan view of the suture lock of FIG. 1;

FIG. 3 is a side elevational view of the suture lock of FIG. 2;

FIG. 6 is a schematic view of the apparatus which may be used in endosurgery with a general indication of the locations which may be appropriate under the circumstances;

FIG. 7 is an enlarged fragmentary perspective view of an incision area and the apparatus of this invention showing how the apparatus is used to close an incision or approximate remote tissues;

FIG. 8 is an enlarged perspective view of a tool used in mounting the suture lock of this invention in preparation for its insertion into the abdominal cavity through an endoport; and FIG. 9 is a fragmentary view of an alternative embodiment for the mounting of the suture lock on the end of the tool.

DESCRIPTION OF THE PREFERRED EMBODIMENTS

Figure 4:
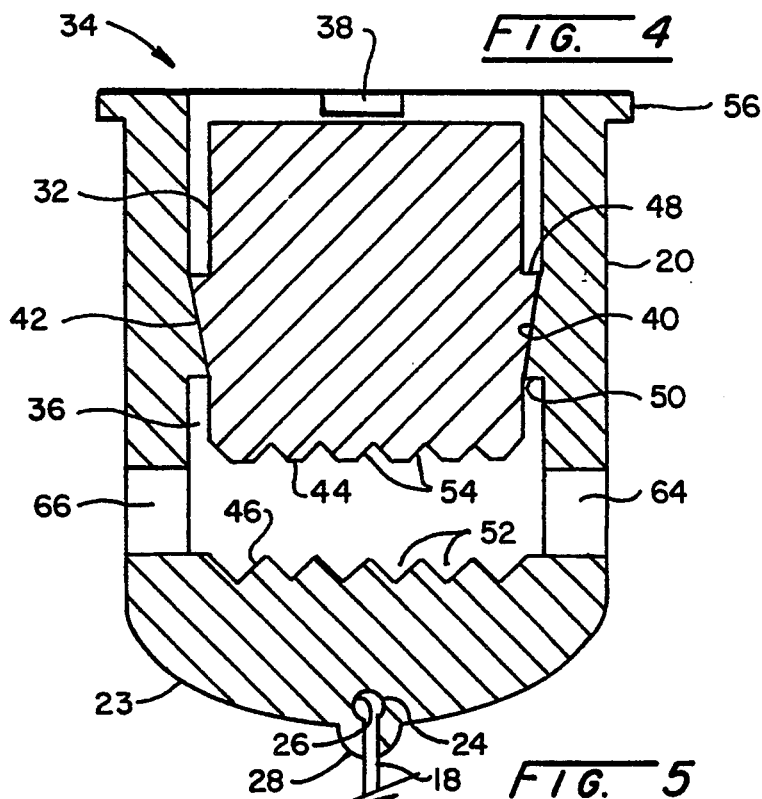
FIG. 4 is a fragmentary sectional view taken along line 4—4 of FIG. 1 with the suture lock in unlocked position.

FIG. 6 shows a human body 10 penetrated by a plurality of endoports 12 to allow endosurgery to be performed within the abdomen. Endoports 12 are small tubes having an internal diameter of 10–12 millimeters and the surgery is performed by a surgeon using a camera and lighting system 14 to allow the surgery area to be observed on a television monitor. The actual work is either remove or reconstruct tissues within the body. Wounds created need to be closed or reconstructed tissues need to be held together. This invention is concerned with the apparatus and procedural steps for suturing the incision.

Looking now to FIG. 1, a suture 18 has one end attached to a housing or cylinder 20 and the other end is attached to a needle 22. Needle 22 includes a conventional hook at the pointed end, but the shape is not critical to this invention.

The housing 20 includes a beveled or hemispherical closed end 23 to minimize irritation to the surrounding tissue.

Figure 5:
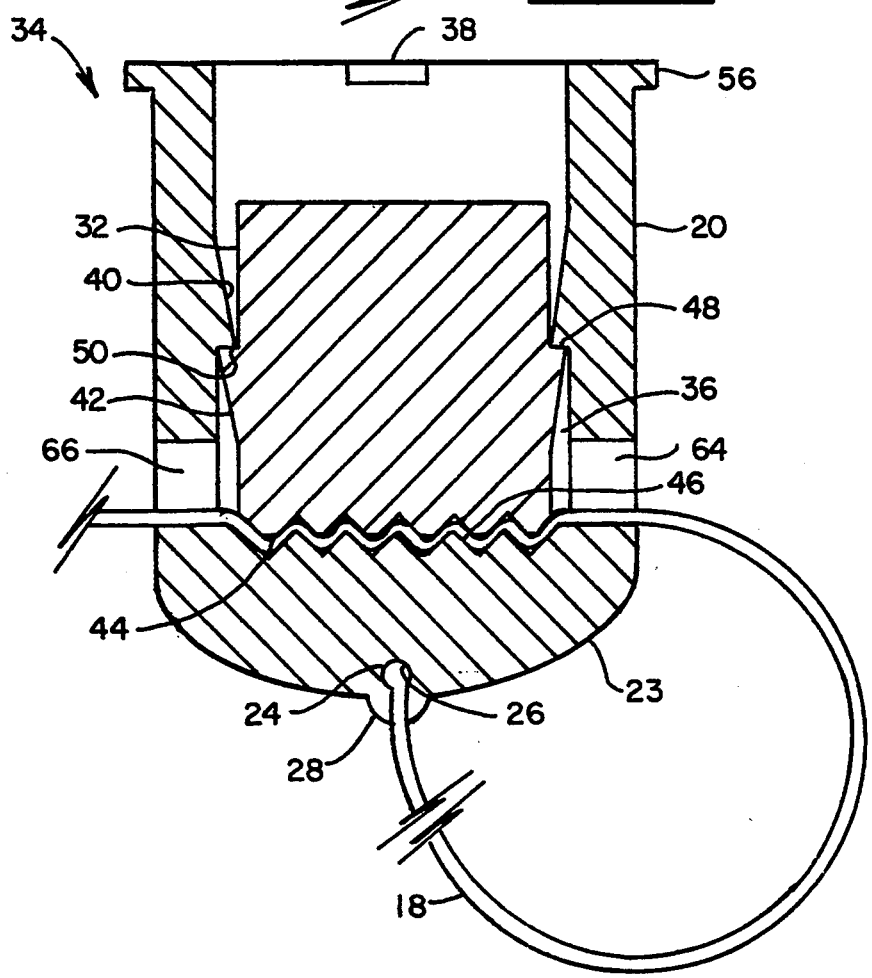
FIG. 5 is a fragmentary sectional view similar to FIG. 4 but at a time after a stitch has been formed to approximate the tissues of a patient and with the piston in depressed or locked position to lock the two ends of the suture in place.

The way the suture is attached to the housing and the needle is not critical to the invention. FIGS. 4 and 5 illustrate the suture 18 having an enlargement 24 secured within an opening 26 in a boss 28 formed integral with the bottom exterior surface 23 of the housing 20.

The means for securing the end of the suture 18 to the housing 20 could include a knot on the end of the suture and the suture could pass through an opening in the bottom or sidewall of the housing with the knot having a greater diameter than the passage. Alternatively, the end of the suture 18 may be attached in some similar fashion to the piston 32. The way the attachment is made is not critical so long as the end of the suture is securely attached to the suture lock 34.

FIGS. 4 and 5 show the suture lock 34 in section. The combination of elements defining the lock consists of the hollow housing 20 having a cavity 36 therein and with a reciprocal piston 32 mounted within the cavity.

Piston 32 is initially held in the upper part of cavity 36 and prevented from falling out of the cavity by a pair of inwardly projecting ears 38, best seen in FIG. 2. Cavity 36 and piston 32 are illustrated as being square in shape and this is the preferred structural feature, but the shape is not critical to the operation of the inventive concept. The cavity and cooperatively shaped piston could be circular, polygonal, oval or any other shape without departing from the inventive concept.

In the unlocked position illustrated in FIG. 4, the piston 32 is held in the upper portion of cavity 36 by cooperatively shaped sloping surfaces 40 and 42 on the housing and piston, respectively.

FIG. 5 illustrates the suture lock 34 with the piston 32 crimped into locking position with its lower surface 44 trapping the needle end of the suture against the bottom inside surface 46 of the housing 20. In this position the piston is locked into place and prevented from retracting in cavity 36 by frictionally engaging shoulders 48 and 50 on the surfaces of the piston and the cavity side of the housing, respectively.

It will be observed that the bottom surface 46 of housing cavity 36 includes a plurality of serrations or grooves 52 and that the lower surface 44 of the piston includes cooperatively shaped ridges 54 to fit into grooves 52 in the locked position illustrated in FIG. 5. Note that the grooves 52 are generally V-shaped and extend transversely of the diagonal passage through the housing. The ridges 54 are V-shaped with the points of the V cut off such that the cut off points provide twice the number of angular engagements for the suture when the piston is pressed into operative position as illustrated in FIG. 5. The need for an increased number of friction points or change in direction crimps in suture 18 is that the suture diameter is very small and its composition makes its surface somewhat slippery. The serrations 52, 54 may take other forms but the trapping feature of mating ridges and grooves is preferred.

The two shoulders 50 in cavity 36 define an aperture between the upper and lower cavity parts. The width of said aperture is less than the width of the combined width of piston 32 and its associated shoulders 48, when the piston and housing are coaxially aligned.

The preferred embodiment for the exterior housing shape includes an outwardly extending flange 56 and its purpose is to provide a gripping area for the support tool illustrated in FIG. 8. Tool 16 mounts the housing 20 in a generally C-shaped slot and of a configuration and proper dimension to allow the mounted housing and tool to slide down an endoport 12. Thereafter the tool 16 and suture lock 34 are manipulated into proper position for forming the stitch, see FIG. 7.

In operation, appropriate endoports 12 are located in conventional fashion and a wound 60 must be closed or tissues approximated. Looking particularly to FIGS. 6 and 7, tool 16 is passed through an endport into close proximity to the incision 60 with the suture lock 34 mounted on the inner most end of the tool 16. Lock 34 carries suture 18 and needle 22 with it into the abdominal cavity upon the insertion of the tool 16. Thereafter allegator grips or needle drivers 62 grasp the needle 22 and push it through the side edges of the incision 60. Then the needle 22 is passed through a first suture pass 64 (best seen in FIGS. 4 and 5) diagonally in a passage through the cavity 36 and out through a second suture pass 66 in the opposite sidewall of housing 20. After the proper tension is drawn on the suture 18, scissor handles 58 on tool 16 (best seen in FIG. 8) are manipulated to retract a cable 68 and thereby rotate lever arm 70 about pivot pin 72. As arm 70 pivots it depresses piston 32 deeper into cavity 36 and traps the needle end of suture 18 between the lower surface 44 of the piston and the inside bottom surface 46 of the housing. Thereafter the needle 22 may be severed from the suture 18 and removed from the cavity by one of the allegator clamps 62.

Note will be taken that in order for the piston to slide downwardly in cavity 36, engaging surfaces 40 and 42 must flex. Either the sidewall of housing 20, the sidewall of the piston 32 or both must deform to allow shoulders 48, 50 to pass. The piston is illustrated as being a solid piece, it could be hollow. A plurality of vertically extending slots 73 could be formed in the sidewall of housing 20 to facilitate its outward flexing to allow the shoulders 48 and 50 to slide past each other as the piston is depressed. Then the housing sidewalls spring back into place to frictionally lock the shoulders 48, 50 together and lock the suture 18 in place inside the cavity between the bottom 44 of the piston and the bottom inside surface 46 of the housing.

Note should also be taken that the first suture pass 64 may be of a smaller size than the second suture pass 66 because the first suture pass will have a better exposed opening than the second suture pass 66. The wider second suture pass facilitates the passage of the hooked needle through the housing because the second suture pass 66 is on the blind side of the housing not easily visible by the camera and the television monitor.

After the piston 32 has been depressed into operative position as illustrated in FIG. 5 and the severed needle removed, further manipulation of scissor handles 58 will eject suture lock 34 from the end of tool 16 and tool 16 may be removed leaving the suture lock in the abdominal cavity.

FIG. 9 illustrates an alternative embodiment for suture lock 34 mounted generally coaxially as a plug in the end of tool 16 and the operative feature is illustrated generally as a rod 74 which may be used to coaxially depress piston 32 to lock the suture 18 in place. Thereafter, the suture lock 34 may be ejected longitudinally by a further gripping of the scissor handles to further push the rod 74 in a coaxial direction which will pop the lock out of the tool.

One other point that deserves mention is the ability of this system to actually "winch" tissues together. Normally in laparoscopic surgery it is difficult to approximate tissue edges if only for the limited number of instruments that can enter the body at one time. With the lock system of this invention the tissues can be approximated by simply pulling on the needle end of the suture once it is placed into both tissues and through the housing.

Having thus described the invention in its preferred embodiments, it will be clear that other modifications may be made without departing from the spirit of the invention. Also the language used to describe the inventive concept and the drawings accompanying the application to illustrate the same are not intended to be limiting on the invention. Rather it is intended that the invention be limited only by the scope of the appended claims.

I claim:

1. An intracorporeal laparoscopic suture and lock including,
    a suture having a needle secured to one end and a suture lock secured to the other end,
    said suture lock comprising a housing and a piston, said piston being mounted to move into a cavity in said housing, said cavity being defined by a sidewall and a bottom,
    two openings in said sidewall, said openings being spaced apart and configured to receive said needle in a passage extending through said cavity and both openings,
    said piston being movable into engagement with said bottom to clamp said suture against said bottom after said needle has passed through both openings.

2. The suture and lock of claim 1 including serrations on said housing bottom to further enhance said clamp of said suture between said piston and said bottom.

3. The suture and lock of claim 2 including serrations on said piston to further enhance the locking ability of said clamp of said suture between said piston and said housing bottom.

4. The suture and lock of claim 1 including a groove in said bottom extending transversely of said passage,
    a ridge on said piston being aligned to enter said groove and clamp said suture against transverse movement after said needle has passed through said cavity and both openings.

5. The suture of claim 4 wherein said groove is generally V-shaped and said ridge is of a mating V-shape with the apex of the ridge V-shape being cut off.

6. The suture of claim 5 including a plurality of parallel V-shaped grooves and a plurality of parallel cut off V-shaped mating ridges.

7. The suture of claim 1 including a friction lock between said sidewall and said piston to prevent relative displacement after said piston has clamped said suture against said housing bottom.

8. The suture of claim 7 wherein said friction lock comprises oppositely facing first and second shoulders, said first shoulder extending from said sidewall toward said piston, said second shoulder extending from said piston toward said sidewall.

9. The suture of claim 8 wherein said piston and cylinder have coaxially aligned axes while said suture is clamped against said bottom,
    said first shoulder defining an aperture leading to said cavity, said aperture having a width perpendicular to said axes which is less than the width of said piston and second shoulder.

10. The suture of claim 9 including a deformable wall in one of said piston or sidewall to allow said shoulders to slip past each other during a clamping process and preventing relative axial movement after said clamping.

11. The suture of claim 10 wherein at least one of said shoulders includes a surface inclined at an angle to said axes,
    each shoulder including a surface extending in a direction perpendicular to said axes.

12. The suture of claim 7 including serrations on said housing bottom to further enhance said clamp of said suture between said piston and said bottom.

13. The suture of claim 10 including serrations on said piston to further enhance the locking ability of said clamp of said suture between said piston and said housing bottom.

14. The suture of claim 7 including a groove in said housing bottom extending transversely of the alignment of said openings,
    a ridge on said piston aligned to enter said groove and clamp said suture against transverse movement after said needle has passed through said cavity and both openings.

15. The suture of claim 14 wherein said groove is generally V-shaped and said ridge is of a mating V-shape with the apex of the ridge V-shape being cut off.

16. The suture of claim 15 including a plurality of parallel V-shaped grooves and a plurality of parallel cut off V-shaped mating ridges.

17. A process for intracorporeal laparoscopic suturing comprising,
    providing a combined piston, cylinder and crimping tool connected together in operative position, one of said cylinder or piston being connected to one end of a suture, a needle being connected to the other end of the suture,
    passing said needle through tissues to form a stitch,
    passing said needle through openings in said cylinder and deploying said suture between the bottom of said cylinder and said piston,
    depressing said piston with said crimping tool to clamp said suture between said bottom and said piston, and
    disengaging said crimping tool from said cylinder.

18. The process of claim 17 including drawing said tissues into desired approximation by placing said suture in tension prior to depressing said piston.

19. The process of claim 18 including locking said piston against relative movement with said cylinder to maintain said suture in frictional engagement with said piston and cylinder bottom.

20. The process of claim 18 including severing said needle from said suture.

* * * * *